(12) United States Patent
Hohenberg

(10) Patent No.: US 6,440,086 B1
(45) Date of Patent: Aug. 27, 2002

(54) BIOPSY NEEDLE

(75) Inventor: Heinz Hohenberg, Hamburg (DE)

(73) Assignee: Leica Mikrosysteme AG, Vienna (AT)

( * ) Notice: Subject to any disclaimer, the term of this patent is extended or adjusted under 35 U.S.C. 154(b) by 0 days.

(21) Appl. No.: 09/715,118

(22) Filed: Nov. 20, 2000

(30) Foreign Application Priority Data

Nov. 19, 1999 (CH) .............................................. 2132/99

(51) Int. Cl.$^7$ ................................................. A61B 5/00
(52) U.S. Cl. ..................................................... 600/567
(58) Field of Search ............... 600/564–656; 606/167, 170

(56) References Cited

U.S. PATENT DOCUMENTS

| | | | |
|---|---|---|---|
| 3,683,891 A | * 8/1972 | Eskridge et al. | ............ 600/564 |
| 4,643,196 A | 2/1987 | Tanaka et al. | .............. 128/753 |
| 4,702,260 A | * 10/1987 | Wang | ......................... 600/564 |
| 4,745,919 A | * 5/1988 | Bundy et al. | ................ 600/564 |

FOREIGN PATENT DOCUMENTS

EP 0 853 238 7/1998

OTHER PUBLICATIONS

H. Hohenberg et al., "High–pressure freezing of tissue obtained by fine–needle biopsy", J. of Microscopy, vol. 183, Pt. 2, pp. 133–139, Aug. 1996, The Royal Microscopical Society.

* cited by examiner

*Primary Examiner*—Max Hindenburg
(74) *Attorney, Agent, or Firm*—Foley & Lardner

(57) ABSTRACT

A precision biopsy needle for removing liquid-containing tissue samples. The needle includes a needle body that receives a tissue sample and an internal plunger that is movable inside the needle body. A removable sample receiving element is introduced between the inner wall of the needle body and the movable inner plunger. The tissue sample may be transferred without the risk of damage to the tissue structure, and prevents the sample material from drying out during manipulation.

19 Claims, 1 Drawing Sheet

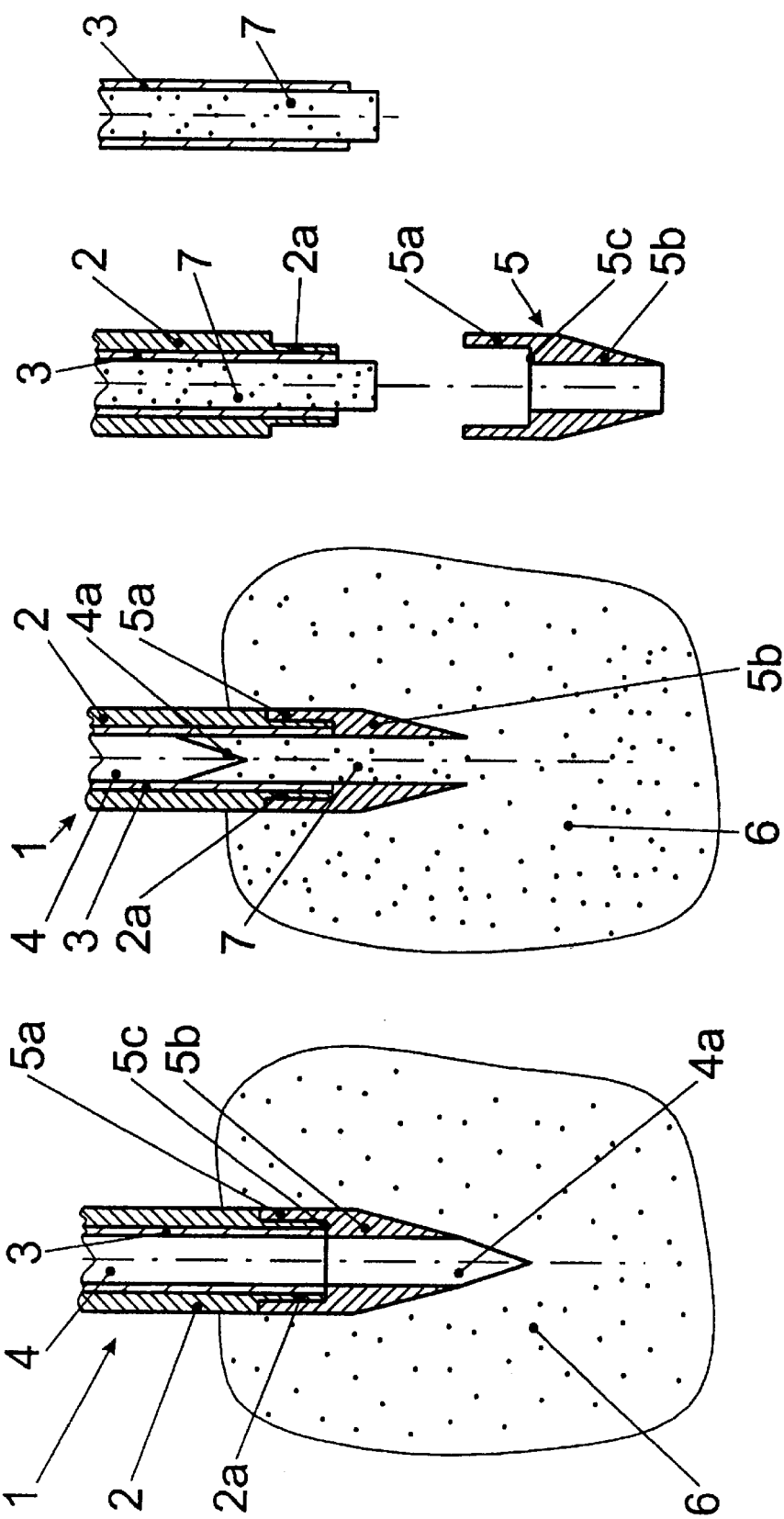

BIOPSY NEEDLE

BACKGROUND OF THE INVENTION

The invention concerns a biopsy needle, in particular a precision biopsy needle, for removing liquid-containing tissue samples. More particularly, the invention is directed to biopsy needles having a hollow needle body that receives the tissue sample and an internal plunger that is movable inside the needle body. The invention further concerns a biopsy apparatus having a hollow needle body for piercing the tissue that is to be biopsied.

Conventional biopsy needles, in particular conventional precision biopsy needles, are provided for removing tissue samples from the interior of the body or from the internal region of organs. Precision biopsy needles make it possible to remove tissue biopsy specimens with a very small diameter on the order of approximately 0.5 mm. The removed piece of tissue is usually located in the front region of the needle body, since it is almost impossible to receive more biopsy specimen without damaging the biopsy specimen through compression.

For further processing of the removed tissue sample, for example, in order to fix and embed it, the piece of tissue must be removed from the needle tip.

Especially with precision biopsy samples having diameters of approximately 0.5 mm or less, such removal is problematic due to the small diameter and low inherent strength of most tissues. Manipulation during transfer of the small pieces of tissue is also critical because of the risk of damage to the large- and small-scale tissue structure, for example, if a tweezers or other mechanical aid is used. There also exists the danger than the small-volume sample material might dry out during manipulation.

SUMMARY OF THE INVENTION

In accordance with one aspect of the invention, there has been provided a biopsy needle for removing liquid-containing tissue samples comprising: a needle body having a first hollow bore section defined by an inner wall, for receiving the tissue sample; an internal plunger axially movable inside the bore section of the needle body; and a hollow, generally cylindrical removable sample receiving element positioned between the inner wall of the needle body bore section and the movable internal plunger.

Preferably, the sample receiving element comprises a hydrophilic material having a high tensile strength, i.e., to permit it to be pulled out of the needle without tearing. The sample receiving element may comprise a porous polymeric material or a cellulose material. The needle body preferably includes a needle head having a cutting edge. The sample receiving element is preferably configured so that, when it is positioned in the needle body, it serves as a lining and has an inside diameter substantially the same as an inside diameter of the needle head.

Preferably, the needle body includes a pair of openings, through which the sample receiving element may be inserted and removed. The needle head is preferably configured to be separated from the rest of the needle body. The inside diameter of the needle head near the cutting edge is slightly smaller than the inside diameter of the sample receiving element. wherein the internal plunger includes a tip for cutting the tissue to be penetrated.

In an alternative embodiment, a biopsy apparatus is provided. The apparatus includes a hollow needle body for piercing a tissue to be biopsied. The needle body includes an internal cavity for receiving a removable sample receiving element. The sample receiving element preferably comprises a material having a high tensile strength. The sample receiving element also preferably comprises a hydrophilic material. In a preferred arrangement, the sample receiving element comprises an expandable or liquid swellable material.

In accordance with another aspect of the invention, there has been provided a method for taking a liquid-containing biopsy tissue sample, comprising: positioning a hollow, generally cylindrical removable sample receiving element into a needle body having a first hollow bore section defined by an inner wall, along the inner wall of the needle body bore section; inserting the needle body into the tissue region from which the sample is desired; relatively moving the needle body and an internal plunger axially movable inside the bore section of the needle body to draw into the sample receiving element a sample of tissue; withdrawing the needle from the tissue; and removing the sample receiving element and sample contained therein from the needle body.

BRIEF DESCRIPTION OF THE DRAWINGS

Further features, advantages, and details of the invention will now be described further with reference to the drawings, which depict an exemplary embodiment and are briefly described below:

FIG. 1 is a schematic representation of a cross section of a receiving region of a biopsy needle that is inserted into a tissue in a position immediately prior to removal of a sample of tissue;

FIG. 2 is a cross sectional view of the receiving region of the biopsy needle during the biopsy procedure;

FIG. 3 is cross sectional view through the separated portions of the biopsy needle that form the receiving region, after tissue sample removal has occurred and the needle has been moved outside the tissue; and FIG. 4 is a cross sectional view through the portion of the biopsy needle containing the removed tissue.

DETAILED DESCRIPTION OF THE PREFERRED EMBODIMENTS

It is the objective of the invention to solve the problems discussed above such as, for example, to allow the transfer of the removed tissue samples to be accomplished without risk of damage to the tissue structure and without risk of excessively rapid desiccation.

This objective is achieved, by providing a biopsy needle having a needle body and a removable sample receiving element that is introduced between the inner wall of the needle body and a movable inner plunger. In an alternative embodiment, a biopsy apparatus is provided that achieves this purpose by providing a needle body that includes, in its cavity, a receptacle for a removable sample receiving element.

According to the invention, therefore, the tissue sample is introduced by way of the biopsy procedure into a sample receiving element that is located inside the biopsy needle and is removable from the needle. The fact that the sample receiving element is removed along with the tissue sample eliminates, during transfer, the manipulation with tweezers or other mechanical aid. This greatly reduces the risk of damage to the tissue structure. The use of a sample receiving element for enclosing the tissue sample ensures that even small-volumes of tissue sample material do not dry out during manipulation.

The invention provides the further advantage of facilitating the preparation of the removed tissue sample in accordance with the method disclosed in EP-A-0 853 238, which (as well as any of its English language counterparts) is incorporated herein by reference, in which tissue samples are freeze-fixed under high pressure. In order to accomplish high-pressure freezing, the tissue sample, contained in the sample receiving element, need only to be introduced into a metal capillary and then attached to the corresponding receiving devices of a pressure transfer circuit of a known high-pressure freezing system. The invention also makes it possible to obtain biopsy samples with a diameter of 0.2 mm and less.

In a preferred embodiment of the invention, the sample receiving element is made of a material that is hydrophilic and/or strong in tension. By taking up liquid from the tissue sample, the material swells slightly, thus slightly increasing the diameter of the sample receiving element. The sample receiving element thus conforms more tightly to the inner wall of the needle body. The smooth, liquid-saturated inner surface of the sample receiving element reduces friction as the tissue sample is received.

A porous polymeric material, in particular cellulose, has proved particularly suitable as the material for the sample receiving element. Cellulose not only has the desired properties but is also a biocompatible material. In addition, cellulose can be easily sterilized.

According to a further feature of the invention, the needle body is equipped with a needle head that includes a peripheral cutting edge. As a result, during the biopsy procedure the tissue sample is cut out in such a way that it can easily slide into the needle body and into the sample receiving element.

According to the present invention, the needle body is configured so that the sample receiving element is introduced into the needle body as a lining thereof. Preferably, the inside diameter of the sample receiving element corresponds substantially to the inside diameter in the needle head region.

The biopsy needle is also advantageously configured such that the sample receiving element can be introduced into the needle body from one of two directions, and can be removed from the needle body in one of two directions. Introduction and removal of the sample receiving element by way of the end equipped with the needle head may be easily accomplished because the needle head is configured to be removable from the needle body.

In a further embodiment of the invention, the inside diameter of the needle head in the region of its cutting edge is slightly smaller than the inside diameter of the sample receiving element. The removed sample thus has a diameter somewhat smaller than the inside diameter of the sample receiving element. As a result, the tissue sample is not affected by swelling of the material of the sample receiving element.

In a further advantageous embodiment, the internal plunger is equipped with a tip that cuts or slits the tissue that is to be penetrated thereby largely preventing damage to surrounding blood vessels.

The biopsy needle 1 depicted in FIGS. 1 through 3 is a precision biopsy needle that is suitable for removing tissue samples having a very small diameter such as, for example, on the order of 0.5 to 0.2 mm. The invention concerns the region of the biopsy needle 1 with which and where the tissue sample is received, so that only this receiving region is depicted in FIGS. 1 through 3. The other regions or parts of biopsy needle 1, including in particular the mechanism for actuating it, are not depicted and may be configured in conventional fashion. U.S. Pat. No. 4,643,196 (incorporated by reference herein) depicts a known biopsy needle configuration.

As shown in particular by FIG. 1, the biopsy needle 1 comprises a cylindrical and internally hollow needle body 2 made of a suitable material, preferably surgical steel. The wall thickness of needle body 2 is on the order of 0.02 to 0.03 mm. The free end region of the needle body 2 has a shaft 2a having an outside diameter that is smaller than the diameter of the remainder of the needle body 2. This may be seen clearly in FIG. 3. Introduced into the interior of the needle body 2 is a sample receiving element 3. The sample receiving element 3 is in contact with the inner wall of the needle body 2 over a certain length and is configured in the form of a capillary, which lines the inner wall of the needle body 2. The sample receiving element 3 is discussed below in further detail.

Resting on the end of the needle shaft 2a is a needle head 5 that includes a hollow cylindrical part Sa and a frustoconical part 5b. The hollow cylindrical part Sa of the needle head S has an outside diameter that corresponds to the outside diameter of needle body 2. The inside diameter of hollow cylindrical part 5a corresponds to the outside diameter of the needle shaft 2a. The longitudinal extension of the needle shaft 2a corresponds to the longitudinal extension of the interior space of the hollow cylindrical part 5a. The bore of hollow cylindrical part 5a transitions, by way of a circumferential step 5c positioned in the interior of needle head 5, into the interior bore of the frustoconical part 5b. The cylindrical interior of the frustoconical part 5b preferably has an inside diameter that is smaller than that of part 5a. The reduction in inside diameter resulting from the step 5c corresponds to the sum of the wall thicknesses of the sample receiving element 3 and the needle shaft 2a. When the needle head 5 is in place, the free ends of the needle shaft 2a and of the sample receiving element 3 rest on the step 5c of the needle head 5. As a result, the interior space of the receiving region of the biopsy needle preferably has a constant diameter, which ensures that a cylindrical internal plunger 4 located in the interior of the needle body 2 can move without impediment.

The internal plunger 4 is made, preferably, of surgical steel. The plunger 4 simultaneously stabilizes the needle body 2 and the sample receiving element 3. In the region of the biopsy needle 1 that is shown, i.e., the receiving region, the internal plunger 4 has a diameter corresponding to the inside diameter of the sample receiving element 3 and the inside diameter of the frustoconical part 5b of the needle head 5. The free end 4a of the internal plunger 4 preferably tapers to a point and, preferably, is configured in stiletto fashion. The position of internal plunger 4, as depicted in FIG. 1, is adjusted and immobilized from outside the biopsy needle 1 by any appropriate means, including conventional means.

The sample receiving element 3 is preferably made of a material having specific advantageous properties which include biocompatibility and hydrophilic properties. In addition, the sample receiving element 3 is preferably made of a material having a high tensile strength, such as found in materials conventionally used in biopsy needle applications. The material is intended to be capable of being cut with tools that are generally used for the processing of biological samples. A porous polymeric material, in particular cellulose, is therefore particularly suitable as a material which meets the above criteria.

The sample receiving element 3 preferably has a wall thickness of approximately 0.001 mm and an inside diameter of approximately 0.2 mm. It can be introduced, selectively from one of the two end regions of the biopsy needle 1, into the interior of the needle body 2.

FIG. 1 shows the receiving region of biopsy needle 1 as it is being advanced to the desired sample removal point. The biopsy procedure can be performed, for example, using ultrasound equipment to precisely locate the end of the needle.

During insertion, the internal plunger 4 remains in the position shown in FIG. 1, and reliably cuts through the tissue 7, until the desired removal point is reached. The plunger 4 prevents the penetration of tissue into the interior of needle body 2.

FIG. 2 shows biopsy needle 1 during reception of the biopsy material, i.e., tissue sample 7, into the interior of the needle 1. After biopsy needle 1 has been advanced to the desired removal point, a mechanism (preferably mechanically driven) causes needle body 2 together with needle head 5 to move forward over a predetermined distance. Internal plunger 4 remains in position relative to tissue 6, while movement is imparted to the sample receiving element 3 together with the needle body 2. The resulting slight negative pressure in the interior of needle body 2 helps to pull the tissue sample material 7, cut out of the tissue 6, into the needle body 2. As a result of the smooth inner surface of the sample receiving element 3, which becomes saturated with liquid from the tissue sample 7, the friction between tissue 7 and sample receiving element 3 is low. Liquid absorption from the tissue sample into the sample receiving element 3 also results in a slight increase in the diameter of sample receiving element 3, so that it conforms tightly to the inner wall of needle body 2.

After the biopsy procedure has ended, the biopsy needle I is removed from the tissue 6, and the sample receiving element 3, filled with tissue sample 7, is removed from the needle body 2. This is done by pulling the sample receiving element 3 out of the needle body 2 in one of the two possible directions. When the element 3 is removed through the needle shaft 2a, first the needle head 5 is pulled off the needle shaft 2a, and then the sample receiving element 3 is pulled out. FIG. 3 shows the needle head 5 already separated from the needle shaft 2a. Tissue sample 7, encased by the sample receiving element 3, is depicted in FIG. 4.

Tissue sample 7 encased by sample receiving element 3 can now be subjected to further preparation. The invention offers, in this context, the particular advantage that the encased tissue sample 7 can be prepared in accordance with the method known from EP-A-0 853 238, in which tissue samples are freeze-fixed under high pressure. For high-pressure freezing, the tissue sample 7 contained in sample receiving element 3 can be introduced into a metal capillary, and connected to the corresponding receiving devices of a pressure transfer circuit of a known high-pressure freezing system . After the freezing procedure, the sample holder along with the sample is stored in liquid nitrogen for further processing.

The method disclosed in EP-A-0853 238 provides for the tissue sample to be introduced into a separate porous capillary that is comparable to sample receiving element 3 of the invention, either by utilizing capillary forces or by gentle suction, while being observed through a stereomicroscope. It has been found in practice that biopsy specimens that have been removed with conventional needles cannot be introduced intact into these capillaries. The invention solves this problem by the fact that the tissue sample 7 is already received during the biopsy procedure into a capillary (i.e. the element 3) that can be used with this method. The biopsy specimen can thus be delivered into the sample holder for freezing by way of a simple transfer.

In a variant of the biopsy needle according to the present invention, the inside diameter of the needle head in the region of its cutting edge is slightly smaller than the inside diameter of the sample receiving element. The removed sample thus has a diameter which is less than the inside diameter of the sample receiving element, thereby permitting swelling of the material of the sample receiving element 3 without compressing the tissue sample.

The invention is not limited to the embodiment depicted. The special and novel aspects include the sample receiving element, which can also be used in the form depicted in other types of biopsy removal units, for example in endoscopic devices, catheters, or the like.

The priority document, Swiss patent application CH 1999 2132/99, is incorporated by reference in its entirely herein.

What is claimed is:

1. A biopsy needle for removing liquid-containing tissue samples comprising:

a needle body having a first hollow bore section defined by an inner wall, for receiving the tissue sample;

an internal plunger axially movable inside the bore section of the needle body; and a hollow, generally cylindrical removable sample receiving element positioned between the inner wall of the needle body bore section and the movable internal plunger.

2. A biopsy needle according to claim 1, wherein the sample receiving element comprises a hydrophilic material.

3. A biopsy needle according to claim 1, wherein the sample receiving element comprises a material having a high tensile strength.

4. A biopsy needle according to claim 1, wherein the sample receiving element comprises a polymeric material.

5. A biopsy needle according to claim 4, wherein the sample receiving element comprises a porous polymeric material.

6. A biopsy needle according to claim 5, wherein the sample receiving element comprises cellulose.

7. A biopsy needle according to claim 1, wherein the needle body includes a needle head having a second hollow bore section and having a forward end configured as a cutting edge surrounding the second hollow bore section.

8. A biopsy needle according to claim 7, wherein the sample receiving element has an inside diameter substantially equal to the inside diameter of the second hollow bore section in the needle head.

9. A biopsy needle according to claim 1, wherein the needle body includes two axial openings, wherein the sample receiving element may be inserted and/or removed through each of the openings.

10. A biopsy needle according to claim 7, wherein the needle head is selectively separable from the rest of the needle body.

11. A biopsy needle according to claim 8, wherein the inside diameter of the second bore section of the needle head near the cutting edge is slightly smaller than the inside diameter of the sample receiving element.

12. A biopsy needle according to claim 1, wherein the internal plunger includes a tip for cutting the tissue to be penetrated.

13. A biopsy apparatus kit comprising:
a hollow needle body for piercing a tissue to be biopsied;
wherein the needle body includes an internal cavity for receiving a removable sample receiving element; and
a plurality of hollow, generally cylindrical removable sample receiving elements for insertion into the internal cavity of the needle body.

14. A biopsy apparatus according to claim 13, wherein the sample receiving element comprises a material having a high tensile strength.

15. A biopsy apparatus according to claim 14, wherein the sample receiving element comprises a hydrophilic material.

16. A biopsy apparatus according to claim 14. wherein the sample receiving element comprises an expandable material.

17. A biopsy apparatus kit comprising:
a hollow needle body for piercing a tissue to be biopsied;
wherein the needle body includes an internal cavity for receiving a removable sample receiving element; and
wherein the internal cavity of needle comprises a first hollow bore section, for receiving the tissue sample, and the needle body includes a needle head having a second hollow bore section, and wherein the first bore section has a diameter larger than said second bore section.

18. A method for taking a liquid-containing biopsy tissue sample, comprising:

positioning a hollow, generally cylindrical removable sample receiving element into a needle body having a first hollow bore section defined by an inner wall, along the inner wall of the needle body bore section;

inserting the needle body into the tissue region from which the sample is desired;

relatively moving the needle body and an internal plunger axially movable inside the bore section of the needle body to draw into the sample receiving element a sample of tissue;

withdrawing the needle from the tissue; and removing the sample receiving element and sample contained therein from the needle body.

19. A method as claimed in claim 18, further comprising inserting the sample contained in the sample receiving element into a metal capillary and high-pressure freezing the sample in the capillary.

* * * * *